_(12)_ United States Patent
Lin et al.

(10) Patent No.: US 8,838,245 B2
(45) Date of Patent: *Sep. 16, 2014

(54) RESPIRATORY STIMULATION FOR TREATING PERIODIC BREATHING

(71) Applicant: Cardiac Pacemakers, Inc., St. Paul, MN (US)

(72) Inventors: Zheng Lin, Torrence, CA (US);
Kenneth C. Beck, Liberty, UT (US);
Jonathan Kwok, Holmdel, NJ (US);
Kent Lee, Shoreview, MN (US);
Yachuan Pu, Laguna Niguel, CA (US);
Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/867,370

(22) Filed: Apr. 22, 2013

(65) Prior Publication Data

US 2013/0238051 A1    Sep. 12, 2013

Related U.S. Application Data

(63) Continuation of application No. 12/249,842, filed on Oct. 10, 2008, now Pat. No. 8,428,711.

(60) Provisional application No. 60/978,975, filed on Oct. 10, 2007.

(51) Int. Cl.
*A61N 1/00* (2006.01)
*A61N 1/36* (2006.01)
*A61B 5/08* (2006.01)

(52) U.S. Cl.
CPC ............ *A61N 1/3611* (2013.01); *A61N 1/3601* (2013.01); *A61B 5/0816* (2013.01)
USPC .................................. 607/42; 607/2; 600/26

(58) Field of Classification Search
USPC ........................................ 607/2, 42; 600/26
See application file for complete search history.

(56) References Cited

U.S. PATENT DOCUMENTS

| 6,240,316 | B1 | 5/2001 | Richmond et al. |
| 6,345,202 | B2 | 2/2002 | Richmond et al. |
| 6,415,183 | B1 | 7/2002 | Scheiner et al. |

(Continued)

FOREIGN PATENT DOCUMENTS

| EP | 01557195 | 7/2005 |
| EP | 01588735 | 10/2005 |

(Continued)

OTHER PUBLICATIONS

"U.S. Appl. No. 12/249,842, Response filed Jul. 25, 2011 to Non Final Offfice Action mailed Mar. 23, 2011", 8 pgs.

(Continued)

*Primary Examiner* — Michael Kahelin
*Assistant Examiner* — Mallika D Fairchild
(74) *Attorney, Agent, or Firm* — Schwegman Lundberg & Woessner, P.A.

(57) ABSTRACT

A system and method for treating and/or preventing is described for treating periodic breathing characterized by cyclical hyperventilation and hypoventilation, examples of which include Cheyne-Stokes respiration and central sleep apnea. The system could also be used in the treatment of other conditions involving an impairment of respiratory drive.

20 Claims, 3 Drawing Sheets

(56) References Cited

U.S. PATENT DOCUMENTS

| | | |
|---|---|---|
| 6,532,959 B1 | 3/2003 | Berthon-Jones |
| 7,082,331 B1 | 7/2006 | Park et al. |
| 7,245,971 B2 | 7/2007 | Park et al. |
| 7,277,757 B2 | 10/2007 | Casavant et al. |
| 8,428,711 B2 | 4/2013 | Lin et al. |
| 2003/0199945 A1 | 10/2003 | Ciulla |
| 2005/0061320 A1 | 3/2005 | Lee et al. |
| 2005/0085734 A1 | 4/2005 | Tehrani |
| 2005/0085865 A1 | 4/2005 | Tehrani |
| 2005/0085866 A1 | 4/2005 | Tehrani |
| 2005/0085867 A1 | 4/2005 | Tehrani et al. |
| 2005/0085868 A1 | 4/2005 | Tehrani et al. |
| 2005/0085869 A1 | 4/2005 | Tehrani et al. |
| 2005/0165457 A1 | 7/2005 | Benser et al. |
| 2005/0240240 A1 | 10/2005 | Park et al. |
| 2005/0251061 A1 | 11/2005 | Schuler et al. |
| 2005/0261747 A1 | 11/2005 | Schuler et al. |
| 2006/0030894 A1 | 2/2006 | Tehrani |
| 2006/0036294 A1 | 2/2006 | Tehrani |
| 2006/0058852 A1 | 3/2006 | Koh et al. |
| 2006/0064137 A1 | 3/2006 | Stone |
| 2009/0099621 A1 | 4/2009 | Lin et al. |

FOREIGN PATENT DOCUMENTS

| | | |
|---|---|---|
| WO | WO-0141868 A1 | 6/2001 |
| WO | WO-2005018737 A1 | 3/2005 |
| WO | WO-2005037077 A2 | 4/2005 |
| WO | WO-2006127366 A1 | 11/2006 |
| WO | WO-2009048610 A1 | 4/2009 |

OTHER PUBLICATIONS

"U.S. Appl. No. 12/249,842, Response filed Feb. 17, 2012 to Final Office Action mailed Oct. 17, 2011", 8 pgs.

"U.S. Appl. No. 12/249,842, Response filed Jul. 25, 2012 to Non Final Office Action mailed Apr. 26, 2012", 10 pgs.

"U.S. Appl. No. 12/249,842, Final Office Action Mailed Oct. 17, 2011", 10 pgs.

"U.S. Appl. No. 12/249,842, Non Final Office Action mailed Mar. 23, 2011", 8 pgs.

"U.S. Appl. No. 12/249,842, Non Final Office Action mailed Apr. 26, 2012", 16 pgs.

"U.S. Appl. No. 12/249,842, Notice of Allowance mailed Nov. 29, 2012", 7 pgs.

"U.S. Appl. No. 12/249,842, PTO Response to 312 Communication mailed Mar. 27, 2013", 3 pgs.

"U.S. Appl. No. 12/249,842, PTO Response to Rule 312 Communication mailed Jan. 14, 2013", 3 pgs.

"U.S. Appl. No. 12/249,842, PTO Response to Rule 312 Communication mailed Mar. 15, 2013", 2 pgs.

"International Application Serial No. PCT/US2008/011641, International Search Report mailed Jan. 21, 2009", 3 pgs.

"International Application Serial No. PCT/US2008/011641, Written Opinion mailed Jan. 21, 2009", 7 pgs.

Cosendai, Gregoire, et al., "A Preliminary Feasibility Study of Different Implantable Pulse Generators Technologies for Diaphragm Pacing System", Neuromodulation, 8(3), (2005), 203-211.

Sasayama, S., et al., "Effects of nocturnal oxygen therapy on outcome measures in patients with chronic heart failure and Cheyne-stokes respiration.", Circ J., 70(1), (Jan. 2006), 1-7.

Sin, D. D., et al., "Effects of continuous positive airway pressure on cardiovascular outcomes in heart failure patients with and without Cheyne-Stokes respiration", Circulation, 102(1), (Jul. 4, 2000), 61-6.

RESPIRATORY STIMULATION FOR TREATING PERIODIC BREATHING

CLAIM OF PRIORITY

This application is a continuation of U.S. patent application Ser. No. 12/249,842, filed on Oct. 10, 2008, now issued as U.S. Pat. No. 8,428,711, which application claims the benefit under 35 U S.C. 119(e) of U.S. Provisional Patent Application Ser. No. 60/978,975, filed on Oct. 10, 2007, each of which is incorporated herein by reference in its entirety.

BACKGROUND

In aerobic metabolism, the body uses oxygen to produce energy and generates carbon dioxide as a metabolic by-product. The physiological purpose of respiration in this regard is to maintain the proper concentrations of oxygen and carbon dioxide in the blood and other body tissues. As blood flows through the lungs, oxygen from inspired air is absorbed into the blood, while carbon dioxide is removed and blown off during expiration. A principal way in which the rhythm of respiration is regulated is through the respiratory center in the brainstem (in the pons and upper medulla). The respiratory center has chemosensitive areas that respond mainly to the concentration of carbon dioxide in the blood. When blood carbon dioxide increases, the respiratory center sends neural signals to the muscles controlling inspiration and expiration to cause an increase in the depth and/or rate of respiration and vice-versa when blood carbon dioxide decreases.

In certain individuals, a dysfunction in the respiratory control mechanism described above produces a pathological condition known as periodic breathing. One type of periodic breathing, Cheyne-Stokes breathing, is characterized by alternating cycles of hyperventilation and hypoventilation. When hyperventilation occurs, the pulmonary blood becomes excessively depleted of carbon dioxide. After some period of time, the pulmonary blood reaches the respiratory control center in the brain and/or respiratory chemoreceptors in the vasculature to cause suppression of respiration. The resulting hypoventilation then causes carbon dioxide in the pulmonary blood to rise excessively. After a transit time to reach the respiratory control center in the brain, the excessive carbon dioxide in the blood causes hyperventilation that starts the cycle again. In normal individuals, the cycles of hyperventilation and hypoventilation as just described do not occur because the transit time for pulmonary blood to reach the brain is short and the carbon dioxide concentration in the tissues is maintained by the circulation in a manner that buffers increases in the carbon dioxide concentration of pulmonary blood. In certain situations, however, the respiratory control mechanism becomes impaired so that Cheyne-Stokes respiration occurs. In patients with heart failure, cardiac output is decreased below normal and blood flow is correspondingly slow, causing the transit time for pulmonary blood to reach the brain to increase. Cheyne-Stokes respiration frequently occurs in heart failure patients and has been shown to be associated with a poorer prognosis and increased mortality. Abnormally elevated chemoreflex sensitivity associated with increased sympathetic activity is another cause of Cheyne-Stokes respiration, and increased sympathetic activity commonly occurs in heart failure patients. Another cause of Cheyne-Stokes respiration is damage to the respiratory control center in the brain that impairs the feedback mechanism for controlling inspiration and respiration. Damage to the respiratory control center can also cause a related condition known as central sleep apnea in which breathing ceases for prolonged periods during sleep.

DETAILED DESCRIPTION

Pathological periodic breathing is characterized by cyclical hyperventilation and hypoventilation, examples of which include Cheyne-Stokes respiration and central sleep apnea. Described herein is a system and method for treating and/or preventing such periodic breathing. The system could also be used in the treatment of other conditions involving an impairment of respiratory drive. Among the possible benefits provided by the system are emergency assistance with breathing, reduction of desaturation, prevention of arousal and associated sympathetic surge, and reversal of respiratory instability, all of which may be especially beneficial for heart failure patients.

Figure 1:
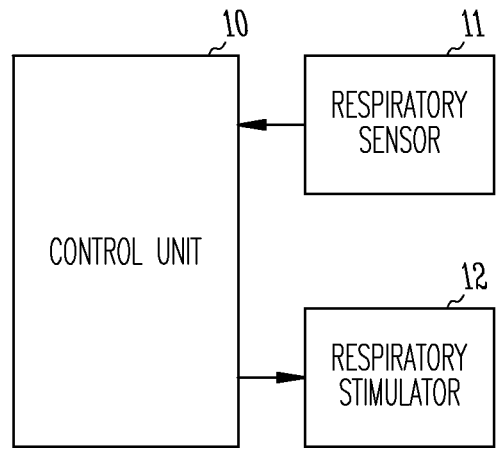
FIG. 1 illustrates an exemplary system for treating periodic breathing.

As illustrated in FIG. 1, an exemplary system includes a control unit 10, one or more respiratory sensors 11 for sensing physiological variables related to the detection or prediction of periodic breathing, and one or more respiratory stimulators 12 for excitatory and/or inhibitory stimulation of neural and/or muscular tissue involved with respiration. The system may be configured to perform a number of different functions as described below, either alone or in combination. One such function involves detection of periodic breathing and then delivering neural and/or muscular stimulation in a manner that counteracts the abnormal breathing pattern. Respiratory activity may be detected by a respiratory sensor that is interfaced to the control unit. The control unit is programmed to deliver the compensatory respiratory stimulation when it recognizes one or more cycles of hyperventilation and hypoventilation from the detected respiratory activity. The respiratory stimulation may be excitatory stimulation of the diaphragm and/or phrenic nerve delivered to augment respiratory drive during hypoventilation or delivered to provide backup ventilation in the case of apnea. Respiratory stimulation may also be delivered as inhibitory stimulation to the diaphragm and/or phrenic nerve in order to diminish respiration during hyperventilation. Such excitatory and/or inhibitory stimulation may be applied during the hypoventilation and hyperventilation phases, respectively, of the cyclical variation in respiratory activity as detected by the respiratory sensor. Excitatory stimulation of phrenic nerves or the diaphragm during the hypoventilation phase may be delivered in an asynchronous manner so as to produce a fixed respiration rate or may be delivered synchronously with detected respiratory activity in a manner that enforces a minimum respiratory rate using an escape interval. The duration of the excitatory and/or inhibitory respiratory stimulation, once triggered by detection of periodic breathing, may be continued for some specified period of time and then restarted if periodic breathing is still detected. Compensatory respiratory stimulation may also be delivered periodically as a preventive measure irrespective of detected respiratory activity.

The respiratory sensor may be one or any combination of sensors that measure physiological variables related to respiration such as transthoracic impedance between external and/or internal electrodes (for measuring minute ventilation and/or cardiac output), chest or abdominal wall motion, phrenic nerve activity, blood pH, blood oxygen concentration, blood carbon dioxide concentration, blood pressure (e.g., pulmonary artery or central venous pressure), activity level and/or body posture via an accelerometer, phrenic nerve activity, airflow in the airway (e.g., the mouth, trachea, or nose), heart sounds, sensed electrical activity (e.g., internal cardiac electrogram, EKG, EEG, or EMG), blood flow, and/or blood circulation time. Physiological variables may also be measured and interpreted by the controller in order to predict the onset of periodic breathing and then initiate delivery of compensatory neurostimulation. For example, a decreased cardiac output such as occurs in heart failure patients is sometimes responsible for Cheyne-Stokes breathing and may be used to predict its onset. Physiological variables may also be measured and interpreted in order to place the detected respiratory activity in the proper context. For example, the magnitude of the compensatory respiratory stimulation may be coordinated to match metabolic demand as determined from measured activity level or heart rate. The system may also be configured to only deliver compensatory respiratory stimulation at appropriate times (e.g., when the patient is sleeping) as determined from the time of day, body posture, heart rate and/or activity level measurements.

The system as described above may be implemented in various ways. The control unit may be an external device adapted to be worn or otherwise disposed near the patient or may be an implantable device. In the latter instance, the control unit may be implanted similarly to a cardiac rhythm management device (e.g., a cardiac pacemaker) or may be incorporated into an implantable cardiac rhythm management device. The respiratory sensors as described above may be external or internal sensors that communicate with the control unit via leads or RF telemetry. Similarly, the respiratory stimulator may be electrodes attached via a lead to an implantable control unit (e.g., an intravenously disposed lead near the phrenic nerve or a nerve cuff electrode) or may be an implantable satellite unit that receives commands (and possibly power) from the control unit via RF telemetry.

Figure 2:
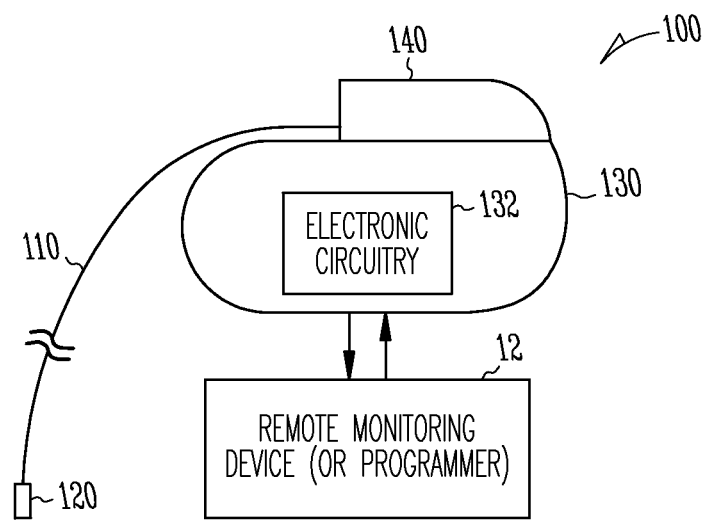
FIG. 2 illustrates an exemplary implantable control unit.

For an embodiment in which the control unit is an implantable device, FIG. 2 shows an exemplary implantable control unit 100 that includes a hermetically sealed housing 130 that is placed subcutaneously or submuscularly in a patient's chest or other convenient location similar to a cardiac pacemaker or ICD. Contained within the housing 130 is the electronic circuitry 132 for providing the functionality to the device as described herein which may include a power supply, sensing circuitry, pulse generation circuitry, a programmable electronic controller for controlling the operation of the device, and a telemetry transceiver capable of communicating with an external programmer or a remote monitoring device 190. An external programmer wirelessly communicates with the device 100 and enables a clinician to receive data and modify the programming of the controller. The housing 130 may be formed from a conductive metal, such as titanium, and may also serve as an electrode for delivering electrical stimulation or sensing. A header 140, which may be formed of an insulating material, is mounted on the housing 130 for receiving one or more leads 110. A lead 110 incorporates one or more electrodes 120 and is adapted to route (e.g., intravenously) the electrode to selected internal locations. The leads electrically connect pulse generation and/or sensing circuitry within the housing to electrodes used for stimulation or sensing. A magnetically or tactilely actuated switch may also be provided that allows the patient to initiate or stop the delivery of respiratory stimulation.

Figure 3:
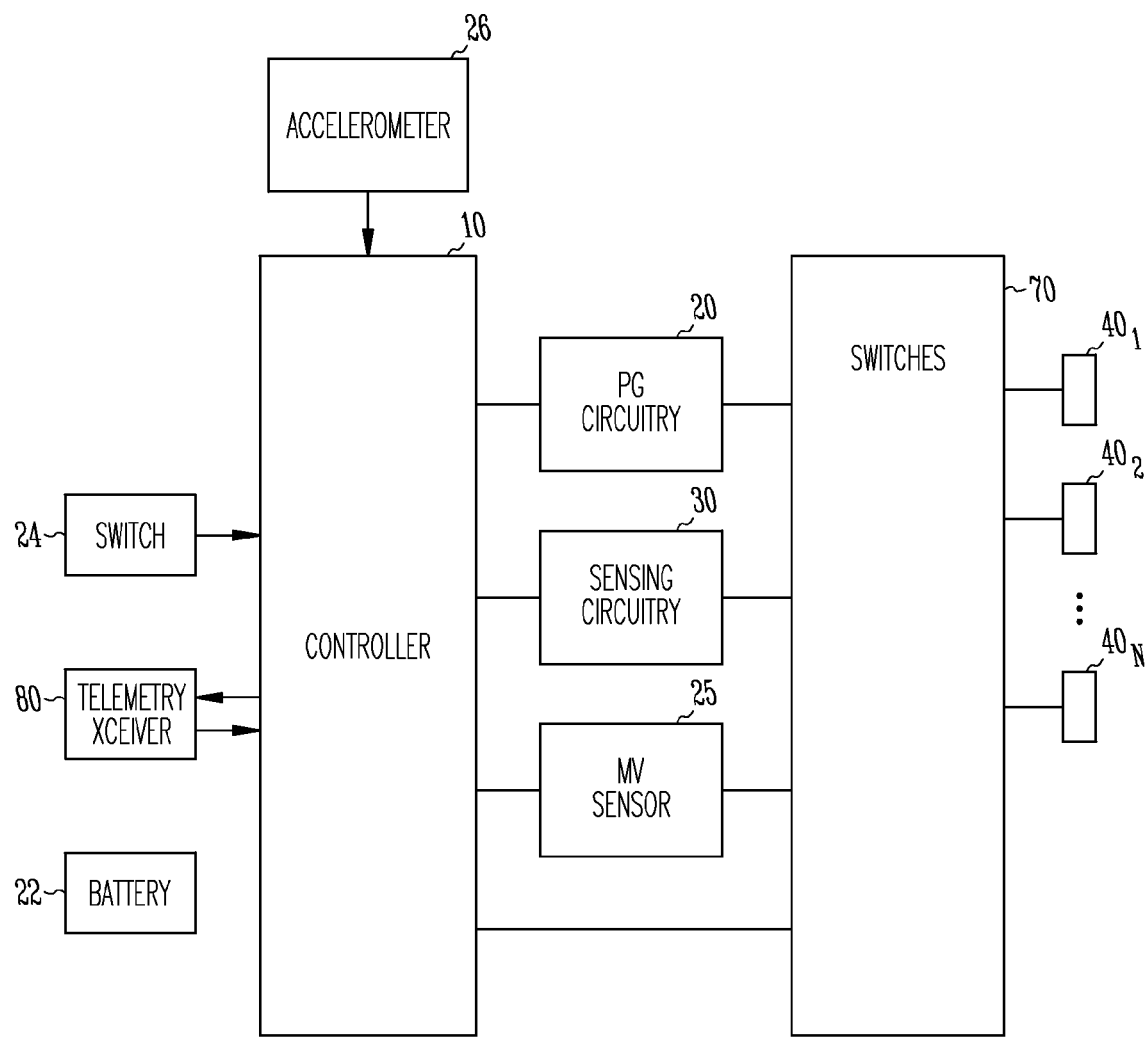
FIG. 3 is a block diagram of exemplary electronic circuitry for sensing respiratory activity and delivering respiratory stimulation.

FIG. 3 is a system diagram of exemplary electronic components contained within the housing 130. A battery 22 contained within the housing provides power to the device. A programmable electronic controller 10 is interfaced to pulse generation circuitry 20 and controls the output of respiratory stimulation pulses. The controller may also be interfaced to sensing circuitry for sensing physiological variables. The controller 10 may be made up of a microprocessor communicating with a memory, where the memory may comprise a ROM (read-only memory) for program storage and a RAM (random-access memory) for data storage. The controller could also be implemented by other types of logic circuitry (e.g., discrete components or programmable logic arrays) using a state machine type of design. As the term is used herein, the programming of the controller refers to either code executed by a microprocessor or to specific configurations of hardware components for performing particular functions. The controller includes circuitry for generating clock signals used to keep track of lapsed time intervals and may also be used to deliver stimulation in accordance with a defined schedule. A telemetry transceiver 80 is interfaced to the controller to enable communication with an external programmer or other external device and allow configuration of selected stimulation and sensing channels after device implantation.

The pulse generation circuitry 20 may be similar to that used in cardiac pacemakers and delivers electrical stimulation pulses through one or more stimulation channels, where a stimulation channel is made up of a pulse generator connected to an electrode. The pulse generation circuitry 20 may include capacitive discharge or current source pulse generators, registers for controlling the pulse generators, and registers for adjusting parameters such as pulse energy (e.g., pulse amplitude and width), polarity, and frequency. Shown in the figure are electrodes $40_1$ through $40_N$ where N is some integer. The electrodes $40_1$ through $40_N$ may be incorporated into unipolar or multi-polar leads. A switch matrix 70 is controlled by the controller and is used to electrically connect selected electrodes to the output of a pulse generator in order to configure a particular stimulation channel. The device may be equipped with any number of pulse generators and electrodes that may be combined arbitrarily to form stimulation channels that may be used by the controller for delivering electrical stimulation to particular sites according to a predetermined schedule and/or in response to sensed conditions. A magnetically or tactilely actuated switch 24 may be provided that is interfaced to the controller 10 and allows the patient to initiate and/or stop the delivery of respiratory stimulation pulses. The pulse frequency, pulse width, pulse amplitude, pulse polarity, burst duration, and bipolar/unipolar stimulation configuration in this embodiment are programmable parameters, the optimal settings of which depend upon the stimulation site and type of stimulation electrode.

The device may also be equipped with different sensing modalities for sensing physiological variables and may be programmed to use these variables in controlling the delivery of respiratory stimulation. The device in FIG. 3 incorporates sensing circuitry 30 that includes sensing amplifiers, analog-to-digital converters for digitizing sensing signal inputs from the sensing amplifiers, and registers that can be written to for adjusting the gain and threshold values of the sensing amplifiers. The switch matrix 70 may be used to connect a particular electrode to a sensing amplifier in order to configure a sensing channel. A minute ventilation sensor 25 employs selected electrodes that are appropriately disposed in the thorax for measuring the impedance across the lungs in order to detect respiratory activity. An impedance sensor with appropriately disposed electrodes may also be used to measure cardiac stroke volume and cardiac output by measuring cardiac impedance. The device may also be equipped with other exertion level sensing modalities that are commonly used in cardiac rhythm management devices such as an accelerometer 26. As noted above, the respiratory stimulator may also be incorporated into an implantable cardiac rhythm management device which has cardiac pacing and/or cardioversion/defibrillation functionality. In that case, the electrodes $40_1$ through $40_N$ may include one or more intra-cardiac electrodes that may be configured into sensing or pacing channels in order to sense and/or pace the atria or the ventricles. The pulse generation circuitry may also include a shock pulse generator for delivering a defibrillation/cardioversion shock via a shock electrode upon detection of a tachyarrhythmia.

Figure 4:
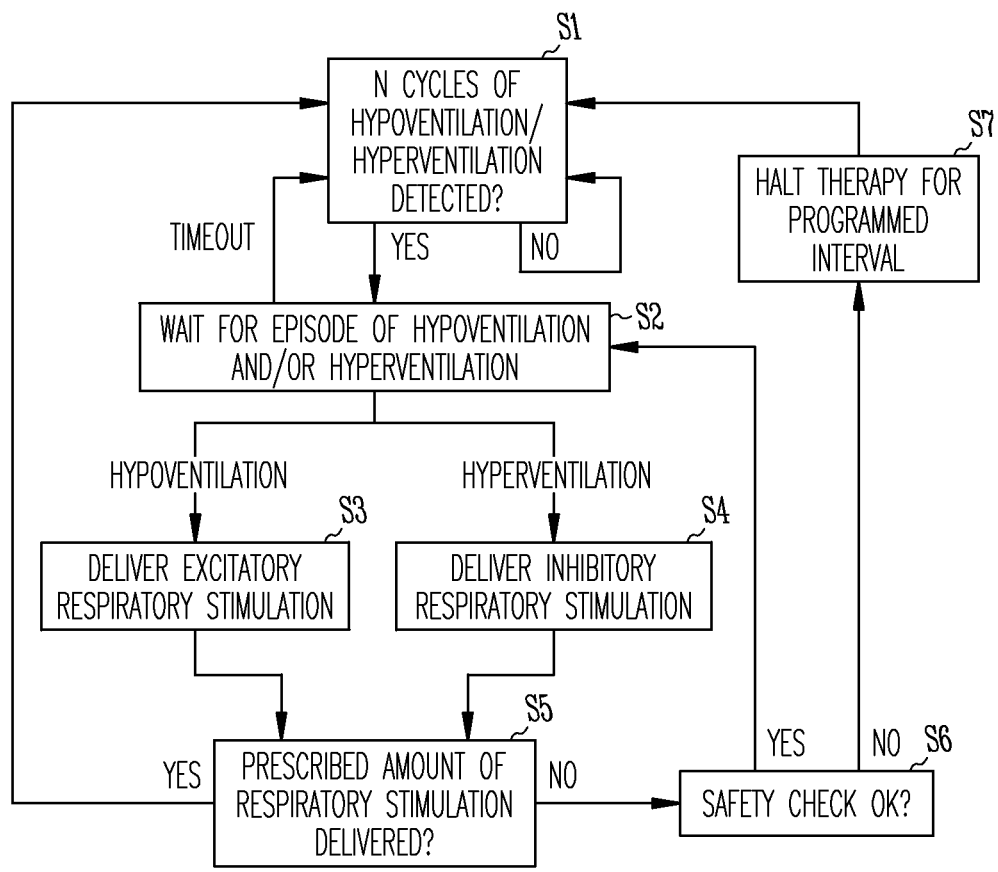
FIG. 4 illustrates an exemplary algorithm for treating periodic breathing.

FIG. 4 illustrates an exemplary algorithm that may be executed by the controller in order to treat periodic breathing. At step S1, respiratory activity is monitored until some specified number N cycles of alternating hypoventilation and hyperventilation are detected indicating periodic breathing. If periodic breathing is detected, the device waits for an episode of hypoventilation and/or hyperventilation at step S2. The device may thus be configured to deliver respiratory stimulation during a hyperventilation episode, a hypoventilation episode, or both. If no episode of hyperventilation or hyperventilation occurs before a specified timeout period, the device returns to step S1 to continue monitoring for periodic breathing. At step S3, the device delivers excitatory respiratory stimulation during an episode of hypoventilation. Such excitatory respiratory stimulation may involve stimulation of the phrenic nerve and/or diaphragm during the inspiratory phase of natural respiration to increase the depth of inspiration and/or stimulation of the phrenic nerve and/or diaphragm in order to increase the frequency of respiration. At step S4, the device delivers inhibitory respiratory stimulation during an episode of hyperventilation in a manner that decreases the depth and/or frequency of respiration. For each of steps S3 and S4, the respiratory stimulation may be delivered, for example, for a specified time period or a specified number of respirations. At step S5, the device determines if the prescribed amount of respiratory stimulation for treating periodic breathing has been delivered. The prescribed amount of respiratory stimulation may be based upon time, quantity of delivered respiratory stimulation pulses, number of hypoventilation/hyperventilation cycles, or other metrics. If so, the device returns to step S1. If not, the device performs a safety check at step S6 that involves determining if:

1) the therapy is actually exacerbating the periodic respiratory pattern, and/or 2) other vital signs from sensors ($CO_2$ level, $O_2$ level, heart rate) are worsening. If the safety check is passed (i.e., the periodic breathing is not being exacerbated and/or other vital signs are not worsening), the device continues to step S2 to continue the therapy. If the safety check is failed, the device proceeds to step S7 where the therapy is inhibited for a programmed interval before returning to step S1. The programmed interval may be set to any predetermined value (e.g., zero or 24 hours) or may specify that therapy is to be inhibited until a specified condition exists such until selected sensed parameters stabilize and return to a specified range, or may specify that therapy is to be inhibited indefinitely until physician intervention.

In certain embodiments described above, reference was made to excitatory and/or inhibitory stimulation of the phrenic nerve and/or diaphragm in order to increase or decrease respiration. It should be appreciated that in those embodiments such stimulation could involve excitatory and/or inhibitory stimulation of other neural and/or muscular tissue involved with respiration (e.g., chest wall muscles or laryngeal muscles) either in addition to, or instead of, stimulation of the phrenic nerve and/or diaphragm.

The invention has been described in conjunction with the foregoing specific embodiments. It should be appreciated that those embodiments may also be combined in any manner considered to be advantageous. Also, many alternatives, variations, and modifications will be apparent to those of ordinary skill in the art. Other such alternatives, variations, and modifications are intended to fall within the scope of the following appended claims.

What is claimed is:

1. A system, comprising:
one or more neurostimulators adapted for disposition near nervous or muscular tissue involved with respiration;
a control unit interfaced to the neurostimulator;
one or more respiratory sensors interfaced to the control nit for detecting respiratory activity;
a cardiac output sensor interfaced to the control unit for measuring cardiac output;
wherein the control unit is programmed to actuate the neurostimulator in response to a decrease in cardiac output predictive of pathological periodic breathing and deliver compensatory respiratory neurostimulation in a manner that counteracts the periodic breathing by delivering excitatory stimulation in order to augment respiration during hypoventilation and delivering inhibitory stimulation in order to diminish respiration during hyperventilation.

2. The system of claim 1 further comprising an accelerometer for measuring activity level and wherein the control unit is programmed to coordinate the magnitude of the compensatory respiratory neurostimulation to match metabolic demand as indicated by the measured activity level.

3. The system of claim 1 wherein the control unit is programmed to:
monitor respiratory activity until some specified number N cycles of alternating hypoventilation and hyperventilation are detected indicating periodic breathing;
if N cycles of alternating hypoventilation and hyperventilation are detected, deliver excitatory respiratory stimulation during an episode of hypoventilation that increases the depth and frequency of respiration and deliver inhibitory respiratory stimulation during an episode of hyperventilation in a manner that decreases the depth and frequency of respiration;
stop delivery of excitatory and inhibitory stimulation after a programmed period of time.

4. The system of claim 1 wherein the respiratory sensor is configured to measure a physiological variable related to respiration as selected from transthoracic impedance between external or internal electrodes, chest or abdominal wall motion, phrenic nerve activity, blood pH, blood oxygen concentration, blood carbon dioxide concentration, blood pressure, activity level and/or body posture via an accelerometer, phrenic nerve activity, airflow, heart sounds, sensed electrical activity, blood flow, and blood circulation time.

5. The system of claim 1 wherein the control unit is programmed to interpret the measurement physiological variables by multiple respiratory sensors, predict the onset of periodic breathing, and deliver compensatory respiratory neurostimulation as a preventive measure.

6. The system of claim 1 wherein the control unit is programmed to only deliver compensatory respiratory neurostimulation when a permitting condition is met, wherein the permitting condition is selected from a specified time of day, a measured activity level being within a specified range, and a sensed body posture being within a specified range.

7. The system of claim 1 wherein the neurostimulator is an implantable satellite unit that receives commands from the control unit via RF telemetry.

8. The system of claim 1 wherein the control unit thriller comprises a magnetically or tactilely actuated switch for starting or stopping delivery of respiratory stimulation.

9. The system of claim 1 wherein the control unit is programmed to perform a safety check that involves determining if the therapy is actually exacerbating the periodic respiratory pattern.

10. The system of claim 9 wherein the control unit is programmed to perform a safety check that involves determining if vital signs are worsening.

11. The system of claim 10 wherein the control unit is programmed to inhibit therapy for a programmed interval if the safety check is failed.

12. The system of claim 11 wherein the programmed interval is set to a predetermined value.

13. The system of claim 11 wherein the programmed interval specifies that therapy is to be inhibited until a specified condition exists.

14. A method, comprising:
    disposing one or more neurostimulators near nervous or muscular tissue involved with respiration;
    disposing one or more respiratory sensors in order to detect respiratory activity;
    measuring cardiac output; and,
    in response to a decrease in measured cardiac output predictive of pathological periodic breathing, actuating the neurostimulator to deliver compensatory respiratory neurostimulation a manner that counteracts the periodic breathing by delivering excitatory in order to augment respiration during hypoventilation and delivering inhibitory stimulation in order to diminish respiration during hyperventilation.

15. The method of claim 14 further comprising coordinating the magnitude of the compensatory respiratory neurostimulation to match metabolic demand as indicated by a measured activity level.

16. The method of claim 14 further comprising:
    monitoring respiratory activity until some specified number N cycles of alternating hypoventilation and hyperventilation are detected indicating periodic breathing;
    if N cycles of alternating hypoventilation and hyperventilation are detected, delivering excitatory respiratory stimulation during an episode of hypoventilation that increases the depth and frequency of respiration and delivering inhibitory respiratory stimulation during an episode of hyperventilation in a manner that decreases the depth and frequency of respiration;
    stopping delivery of excitatory and inhibitory stimulation after a programmed period of time.

17. The method of claim 14 wherein the physiological variable related to respiration as selected from transthoracic impedance between external or internal electrodes, chest or abdominal wall motion, phrenic nerve activity, blood pH, blood oxygen concentration, blood carbon dioxide concentration, blood pressure, activity level and/or body posture via an accelerometer, phrenic nerve activity, airflow, heart sounds, sensed electrical activity, blood flow, and blood circulation time.

18. The method of claim 14 further comprising interpreting the measurement physiological variables by multiple respiratory sensors, predicting the onset of periodic breathing, and delivering compensatory respiratory neurostimulation as a preventive measure.

19. The method of claim 14 further comprising only delivering compensatory respiratory neurostimulation when a permitting condition is met, wherein the permitting condition is selected from a specified time of day, a measured activity level being within a specified range, and a sensed body posture being within a specified range.

20. The method of claim 14 wherein the neurostimulator is an implantable satellite unit that receives commands via RF telemetry.

* * * * *